United States Patent [19]

Smith, Jr. et al.

[11] 4,409,481
[45] Oct. 11, 1983

[54] METHOD FOR SIMULTANEOUS MEASUREMENT OF THERMAL NEUTRON DECAY COMPONENTS

[75] Inventors: Harry D. Smith, Jr.; Ward E. Schultz; Jerry L. Verbout, all of Houston, Tex.

[73] Assignee: Halliburton Company, Duncan, Okla.

[21] Appl. No.: 383,680

[22] Filed: Jun. 1, 1982

Related U.S. Application Data

[63] Continuation-in-part of Ser. No. 182,151, Aug. 28, 1980, abandoned.

[51] Int. Cl.³ .............................................. G01V 5/00
[52] U.S. Cl. .................................... 250/270; 250/262
[58] Field of Search .............. 250/262, 264, 265, 269, 250/270

[56] References Cited

U.S. PATENT DOCUMENTS

| | | | |
|---|---|---|---|
| 3,930,153 | 12/1975 | Scott | 250/270 X |
| 4,122,338 | 10/1978 | Smith, Jr. et al. | 250/270 X |
| 4,152,590 | 5/1979 | Smith, Jr. et al. | 250/270 X |
| 4,157,469 | 6/1979 | Randall | 250/270 X |
| 4,223,218 | 9/1980 | Jacobson | 250/269 X |
| 4,315,148 | 2/1982 | Randall | 250/270 X |

Primary Examiner—Davis L. Willis
Attorney, Agent, or Firm—William J. Beard

[57] ABSTRACT

A method is disclosed for simultaneous determination of borehole and formation thermal neutron decay time components. The methods employ pulsed high energy neutron sources and time gated dual spaced detectors. Exponential decay curves are assumed for each of the components and iterative least squares fitting employing rapid convergence techniques are utilized.

49 Claims, 10 Drawing Figures

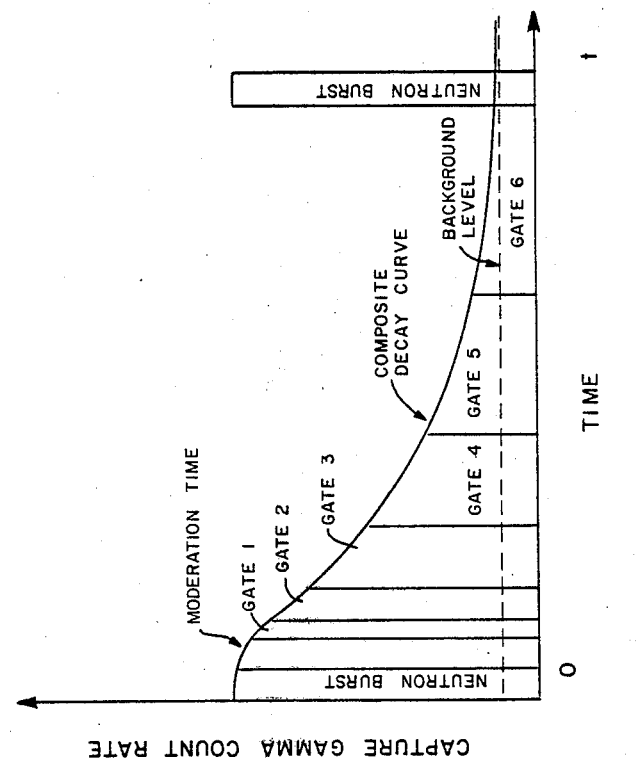
FIG. 5
FIG. 3
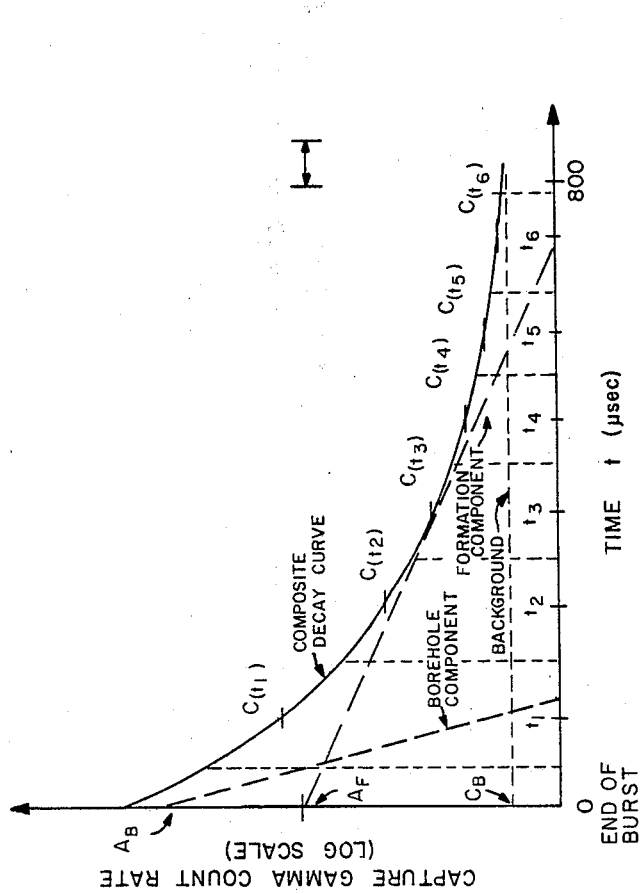
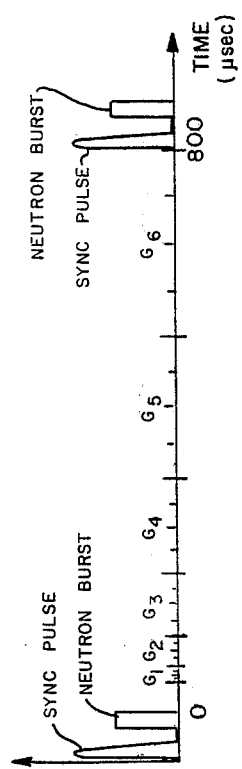
FIG. 6
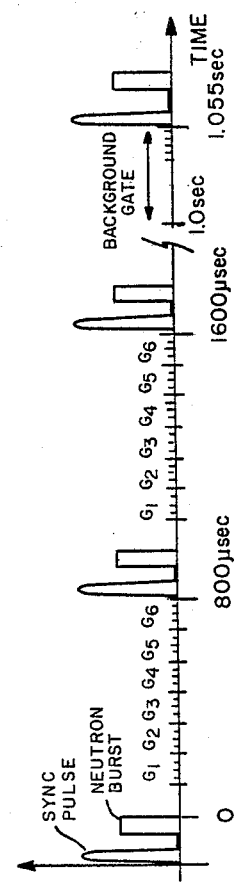
FIG. 4

METHOD FOR SIMULTANEOUS MEASUREMENT OF THERMAL NEUTRON DECAY COMPONENTS

BACKGROUND OF THE INVENTION

This invention relates to in situ measurements of earth formations traversed by a well borehole. More particularly, the invention relates to the measurement of the thermal neutron decay time (or neutron lifetime) of earth formations in the vicinity of a wellbore and of the borehole itself.

The observed decay rate of the thermal neutron population in the vicinity of a well borehole following a pulse or burst of high energy neutrons can be approximated by the sum of formation and borehole exponential terms plus a background term which can vary according to formation and borehole conditions. In typical field conditions the borehole component of the thermal neutron lifetime, or decay time, decays more rapidly than the formation component of thermal neutron lifetime. The primary parameter of interest is $\Sigma_F$, the mean lifetime of thermal neutrons within the formation. Another parameter of interest is $\Sigma_B$, the mean lifetime of thermal neutrons in the borehole. The present invention provides methods and apparatus for determining both of these parameters of interest simultaneously and in real time, and also can measure the relative magnitudes of each component.

The system and methods of the present invention employ a pulsed source of fast neutrons. The fast neutrons are slowed down (or moderated) to thermal energy rapidly by interaction with the nuclei of the elements in the borehole, the earth formations surrounding the borehole, and fluids contained in the pore space of such formations. The thermal neutron lifetime or decay time of the earth formation is largely determined by the salt or chlorine content of the earth formations. The hydrogeneous matter in the pore spaces and borehole rapidly attenuates or slows down the fast neutron flux emitted by a source of pulsed fast neutrons. The fast neutrons when slowed to thermal energy are said to be thermalized and can then be captured by the nuclei of elements comprising the formation matrix and fluids filling the formation matrix and the materials comprising the wellbore, including the borehole fluid, logging instrument, and possibly well casing. The element chlorine, which is found in highly saline borehole fluids and earth formation fluids in the pore spaces of earth formations in the vicinity of a borehole has a very high capture cross-section for thermalized neutrons. Thus a measurement of the thermal neutron decay time or neutron lifetime of earth formations in the vicinity of a well borehole can be indicative of the amount of saline fluids present in the pore spaces of the formation. When combined with formation water salinity, porosity measurements and measurements of formation shaliness, this results in a combination which can be used to discriminate oil and gas from salt water filled pore spaces in the vicinity of a well borehole.

BRIEF DESCRIPTION OF THE PRIOR ART

Two commercially available services for measuring the thermal neutron lifetime or thermal neutron decay time of earth formations in the vicinity of a well borehole are presently available. Both of these commercial techniques employ the assumption that the wellbore materials are of a significantly higher thermal neutron capture cross section than the surrounding earth formations. By making this assumption, then a neutron burst or pulse may be emitted from a well logging instrument situated in the borehole, and after a time delay which is sufficient to allow the thermal neutrons in the well borehole itself to all be substantially captured by the wellbore nuclei having a high capture cross-section, the borehole decay time component may be ignored. Then measurements of the rate of decay of the thermal neutron population in the earth formations may be measured. These commercial neutron lifetime (or thermal neutron decay time) measurements have proven to be particularly valuable in evaluating the producing potential of earth formations in the vicinity of cased well boreholes. In both of these presently available commercial techniques, a well logging instrument which traverses the wellbore uses a pulsed source of high energy (14 Mev) neutrons, usually produced in a deuterium-tritium accelerator tube.

The first commercially available technique, at the present time is known as the "fixed gate" technique. In this technique, the neutron source is repetitively pulsed and for each neutron pulse a cloud of fast neutrons is injected in a generally spherically symmetric fashion about the source into the surrounding earth formations. The fast neutron cloud passes from the well tool through the drilling mud, wellbore casing, cement between the casing and the earth formation surrounding the wellbore and into the earth formations. In this technique, typically each such pulse of fast neutrons has approximately a constant intensity width and lasts typically for a time duration of from 10 to 100 microseconds. The number of thermal neutrons comprising this cloud or population then decays due to the capture of the thermalized neutrons by nuclei in the earth formations and borehole.

After an initial time period following the neutron burst (typically about 300–400 microseconds), during which the resultant capture gamma ray distribution in the borehole, mud and casing is assumed to be substantially dissipated, measurements of the number of thermalized neutrons in the vicinity of the well tool are made during two successive time intervals, or gates, of fixed duration. These two measurements made during the constant time gates or successive time intervals can then be used to define an approximately exponential decay curve for the thermal neutron population in the earth formation surrounding the borehole.

The assumption is made that enough time has passed following the neutron burst for essentially all thermalized neutrons in the vicinity of the wellbore itself to have been captured by the borehole elemental nuclei. The assumption is that the borehole component of the thermal neutron decay or thermal neutron lifetime is generally shorter than the earth formation component of thermal neutron decay or thermal neutron lifetime. This usually occurs when borehole drilling fluids having a high chlorine or salt water content are encountered. However, in boreholes containing air, gas, fresh water or oil this relationship does not always hold, nor does it always hold in casing surrounded by low salinity cement. Accordingly, one particular advantage of the present invention over this "fixed gate" prior art thermal neutron lifetime measuring technique is that no assumption is made as to the relative thermal neutron decay time characteristics of the borehole fluid with respect to the thermal neutron decay time or lifetime characteristics of the earth formations surrounding the borehole.

The thermal neutron population in the formation in the vicinity of the borehole is inferentially measured during the two fixed time gating intervals following each neutron burst or pulse by measuring the capture gamma rays resulting from the capture of thermalized neutrons by the nuclei of materials comprising the earth formations and fluids in the pore spaces therein. The two time intervals or gates most frequently used, for example, in the fixed gate technique for measuring thermal neutron decay times can occur between 400-600 microseconds following the neutron burst and between 700-900 microseconds following the neutron burst. These values are used in typical earth formations regardless of the salinity of the fluid present in the borehole. Since these fixed time gates are designed for general borehole use regardless of salinity they are not optimized as to maximizing count rate. Because the gates are delayed for a relatively long time after the burst, the count rate during the gates is lower than optimum in saline fluid filled boreholes. This can lead to statistical uncertainty in the measurement of $\Sigma$.

If neutron diffusion effects are ignored, the relationship for the decay of a thermal neutron population in a homogeneous medium having a thermal neutron macroscopic capture cross-section $\Sigma$ can be expressed as in Equation 1.

$$N_2 = N_1 e^{-\Sigma(vt)} \qquad (1)$$

wherein $N_1$ is the number of thermal neutrons at a first point in time $t_1$; $N_2$ is the number of thermal neutrons present at a later point in $t_2$; e is the Naperian logarithm base; t is the time between two measurements $(t_2-t_1)$; and v is the velocity of the thermal neutrons. The macroscopic thermal neutron capture cross section $\Sigma$ of a reservoir rock (which can be obtained from Equation 1) is dependent upon its porosity, matrix composition, shaliness, the formation water salinity, and the quantity and type of petroleum contained in the pore spaces therein. This quantity thus represents a valuable physical parameter or measurement of the formation to be obtained.

The second presently commercially available prior art technique for measuring thermal neutron decay time or thermal neutron lifetime uses a reciprocal relationship of the macroscopic thermal neutron capture cross-section $\Sigma$ which is defined in terms of $\tau$ the time constant for absorption of the thermal neutrons. A relationship analoagous to Equation 1 but defined in terms of $\tau$ is given by:

$$N = N_o e^{-t/\tau} \qquad (2)$$

where $\tau = 1/v\Sigma$. In Equation 2, N represents the thermal neutron density at any time t; $N_o$ is the thermal neutron density at an initial time, $t_o$; e again represents the Naperian logarithm base constant; and $\tau$ is the time required for the thermal neutron population to decay to 1/e of its value at $t_o$.

In measuring the thermal neutron decay time using the second prior art technique known as the "sliding gate" arrangement, the well logging instrument emits a pulse or burst of fast neutrons into the formation the duration of which is actually controlled via a feedback loop to measured values of $\tau$ of the earth formations. For example, the neutron pulse duration may be one $\tau$ duration. Gamma ray detectors are used to obtain counts of the capture gamma rays during two successive time intervals following the generation of the neutron cloud in the vicinity of the well borehole in order to define the exponential decay curve. In this technique, however, the two intervals used for measuring the gamma ray population to define the exponential decay curve are not fixed in duraton or in starting time following the neutron burst. The value of $\tau$ measured on the previous neutron burst cycle is used in an iterative feedback circuit to define the neutron burst duration for the generation of the fast neutrons as well as the waiting interval to the opening of the first time gate following the burst, the duration of the first time gate, the duration of the second time gate and the waiting interval between the initiation of the first and second time gates. All of these times are adjusted until a predetermined relationship involving the ratio of counts in the two gates is satisfied, and then $\tau$ is obtained from the resulting time parameter. For example, the second measurement gate duration may be two $\tau$ in duration. A waiting interval of two $\tau$ following the neutron burst maybe used before the opening of the first gate. The first gate may have a duration of one $\tau$.

In both of the above described prior art systems for determining thermal neutron lifetime or decay time, the neutron source and one detector are all that is essential for the measurement. However, in both of the commercially available techniques, dual spaced detectors are employed and measurements at the detectors of the capture gamma radiation due to thermal neutrons are used to generate approximations or measurements of the porosity of the earth formations in the vicinity of the borehole. The system of the present invention also employs two detectors and can make porosity measurements.

As previously discussed, both of the commercially available techniques for measuring thermal neutron decay time at present employ the assumption that the borehole thermal neutron decay time is substantially less than that of the earth formations in the vicinity of the borehole and may thus be discriminated against by "timing out" the borehole component. In sliding gate techniques, at a time intervals substantially following both of the detection gates used for $\tau$ or $\Sigma$ measurements, a background time gate can be used to measure the background including gamma radiation due to neutron activation events in the borehole and earth formations surrounding the wellbore. These background counts are, after appropriate normalization, generally subtracted from the counts made during the two measurement gates in such a system so as to remove the influence of natural gamma ray background which occurs in the vicinity of the well borehole and any activation background which may be induced within the gamma ray detectors and formation by the neutron source. It should be noted that both of the previously described commercial well logging systems do not use all of the possibly available gamma ray count information following each burst of neutrons. The time intervals during which the detectors are not gated to accept information are lost in both these prior art systems. Thus, the full utilization of the neutron output from the neutron generator is not made in the prior art schemes. Similarly, both of the prior art techniques assumes that the formation thermal neutron lifetime or thermal neutron decay time may be essentially completely separated from that of the borehole component by time gating. Even under ideal conditions, this assumption is not completely valid. The present invention utilizes techniques and systems which avoid each of these prior art assumptions and limitations.

BRIEF DESCRIPTION OF THE INVENTION

In the present invention a well logging tool is moved through the borehole and includes a pulsed source of fast neutrons and two radiation detectors. The neutron source generates a pulse of fast neutrons of approximately constant intensity for a duration of between 10 and 100 microseconds. These neutrons are introduced into the media comprising the well borehole and surrounding formations and result in a thermal neutron population being generated from the slowing down of the fast neutrons in the earth formation media and the borehole. After a very short pause to allow moderation of the fast neutrons following the neutron pulse, the detectors are gated on and the capture gamma radiation resulting from the capture of thermal neutrons in the borehole and earth formations in the vicinity of the borehole are recorded essentially continuously until the next neutron burst is about to begin. During multiple time gates which occur during this essentially continuous interval, the capture gamma ray counting rate is observed in four or more (the use of six gates is described in the flow chart which is described below) essentially contiguous time gates. The contiguous nature of the gates tends to reduce statistical errors, however is not essential to the technique as long as the gates employed cover the same overall time span between bursts (ie. there can be gaps between the gates). The multiple time gate measurements of the counting rates are supplied to a thermal neutron lifetime computer which computes the formation and borehole neutron lifetime components by means of iterative and least squares fitting of this count rate data taken during four, or more time gates following each neutron burst. The thermal neutron lifetime computer is enabled to calculate both the borehole thermal neutron lifetime component and the earth formation thermal neutron lifetime component simultaneously. Approximately once per second, and for approximately five percent of the one second operating cycle, the neutron source is turned off and the detectors are used to establish any relatively long lived background counting rate due to source neutron induced gamma ray activity within the gamma ray detector, the formation, borehole, logging sonde, or natural gamma radiation in the vicinity of the borehole. This background gamma ray information is then properly normalized and subtracted from the four or more time gate measurements of thermal neutron capture gamma rays made following each neutron burst. The percentage of the one second cycle used for background can be varied from 5% if desired, as long as proper normalization procedures are used.

Electronic systems are provided in the downhole tool and at the surface for producing the measurement sequence and neutron pulses as described. Additionally, synchronization or sync pulses are also generated to provide a means for separating and synchronizing the counts of gamma rays representative of thermal neutron capture during each of the four or more gating portions of the measurement cycle following each neutron burst, as previously described. Moreover, a surface computer and processing technique therefor for deriving the thermal neutron decay times, or lifetimes, of the borehole component and earth formation components is provided and is attached to a well logging recorder in which a record medium may be moved as a function of borehole depth, while the logging instrument is moved through the borehole. The formation and borehole components of thermal neutron lifetime may be plotted as a function of borehole depth on this recorder. Thus, the system of the present invention includes techniques for determining the value of thermal neutron decay time or macroscopic thermal neutron capture cross-section of the borehole and the surrounding media simultaneously, and also the magnitudes of each decay component.

The invention is best understood by reference to the following detailed description thereof when taken in conjunction with the accompanying drawings, in which:

BRIEF DESCRIPTION OF DRAWINGS

FIG. 3 is a graphical relationship illustrative of the composite thermal neutron population decay curve and time gates according to one embodiment of the present invention.

FIG. 4 is a schematic graphical illustrating a telemetry sequence as a function of time in the present invention.

FIG. 5 is a graphical relationship illustrating the composite thermal neutron population decay curve and time gates according to a second embodiment of the present invention.

FIG. 6 is a schematic representation of a telemetry sequence as a function of time for the gating arrangement of FIG. 5.

DESCRIPTION OF THE PREFERRED EMBODIMENTS

Figure 1:
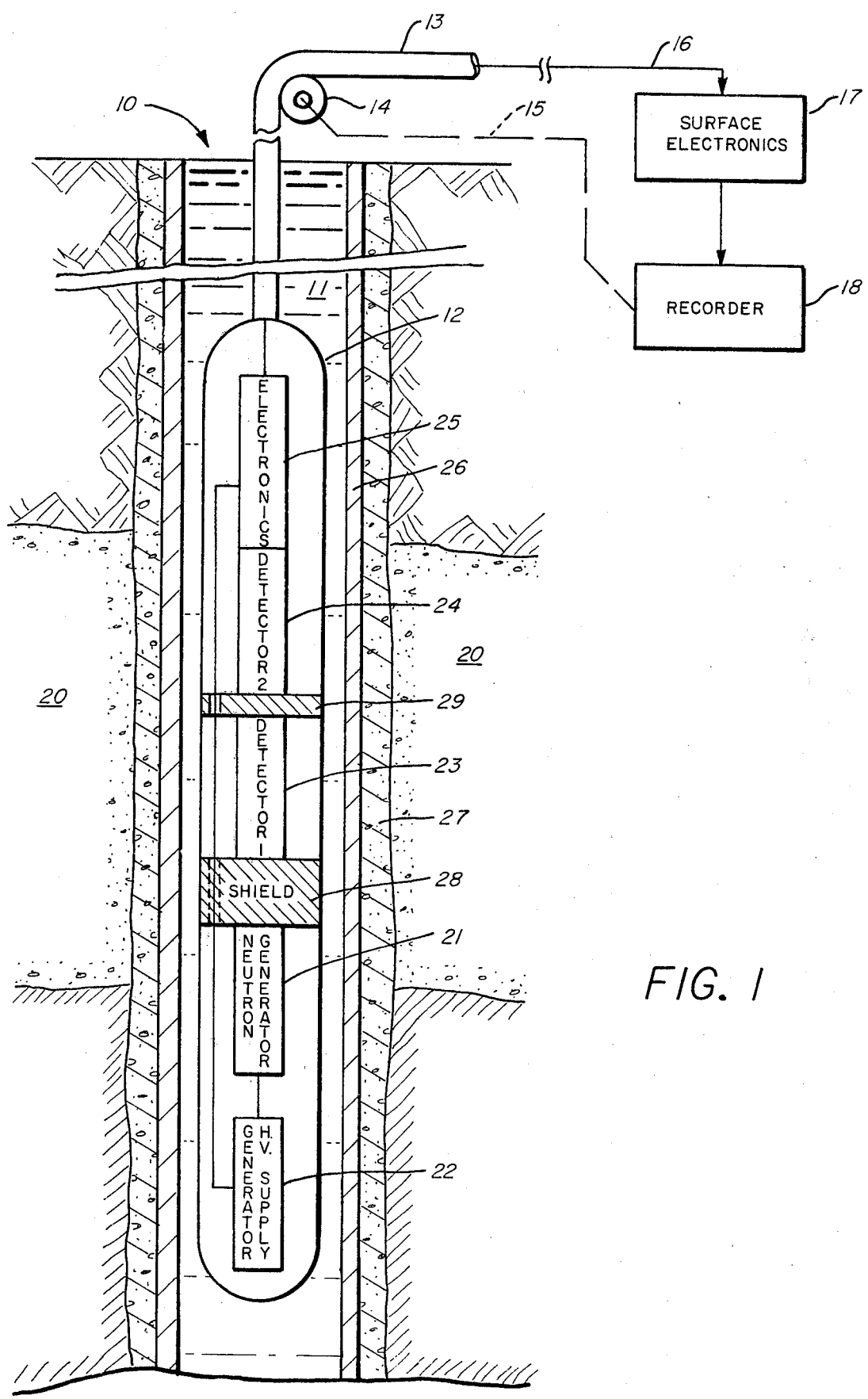
FIG. 1 is a schematic drawing showing a well logging system in accordance with the present invention.

The previously discussed prior art techniques for determining thermal neutron lifetime or decay time can encounter two major problems. These two major problems are: (1) Under certain formation and borehole conditions, the borehole component has not decayed to a negligible level prior to the beginning of the gating of detectors sequence for determining the neutron lifetime. This results in a erroneous measurement of $\tau_F$, and; (2) the statistical accuracy of $\tau_F$ is sometimes quite poor because the decay rate samples have to be taken at relatively long intervals of time after the neutron burst in order to minimize the effects of the borehole component.

A third problem in prior art neutron lifetime logging techniques was first discussed by Mills, et al in a paper entitled "Pulsed Neutron Experiments in a Borehole Model", Mills, et al in Nuclear Science and Engineering, Vol. 21, Pages 346-356 (1965). The Mills, et al paper shows that even if $\tau_F$ is computed from count rate data taken at time delays sufficient for the borehole component to decay to a negligible level, that the computed $\tau_F$ is still a function of $\tau_B$, the lifetime of thermal neutrons within the boreole. This may be thought of as being an interactive term due to thermalized neutrons continuously diffusing back into the borehole from the formation even after the "original" borehole thermal neutron population has decayed by capture to a low level. Thus, the two prior art techniques completely dismiss the effect caused by this third problem since both assume that the formation and borehole are independent of each other. The present invention however takes into account the problems of all three effects and results in a much more reliable measurement of the thermal neutron lifetime or decay time than heretofore has been available.

In order to obtain accurate hydrocarbon saturations from pulsed neutron lifetime or decay time logs. The following three criteria should be met:

(1) $\tau_F$, the observed lifetime of the formation component should be computed from count rate data which contains no contributions from neutron capture within the borehole;

(2) $\tau_F$ should be statistically as accurate as possible; and (3) The intrinsic mean lifetime of the formation component $\tau_{Fi}$ should be determined before hydrocarbon saturation calculations are made.

According to the previously mentioned Mills, et al paper, the measured lifetime can be related to $\tau_{Fi}$, the intrinsic formation lifetime only if borehole parameters are known. It is therefore, desirable to measure both the formation component $\tau_F$ and the borehole component $\tau_B$ of the thermal neutron lifetime or decay time simultaneously for maximum accuracy.

As previously discussed, the observed decay rate of the thermal neutron population in the vicinity of a well borehole following a burst of high energy neutrons may be described as the sum of a formation component, a borehole component and a background component. This may be expressed mathematically as in Equation 3.

$$C(t) = A_B^{-t/\tau_B} + A_F^{-t/\tau_F} + C_B \qquad (3)$$

In Equation 3, C(t) is the counting rate at any time t measured from a reference time. $A_B$ and $A_F$ are constants which may be interpreted according to FIG. 3 of the drawings with $A_B$ representing the initial borehole component at the reference time =0 at the end of the neutron burst, and $A_F$ representing the initial formation component at the reference time =0. These components are shown in FIG. 3 as intercepts on the ordinate axis as a function of time. $\tau_B$ in Equation 3 represents the borehole component of composite lifetime of thermal neutrons. $\tau_B$ may be thought of as the slope of the borehole component curve of FIG. 3. Similarly, $\tau_F$ represents the formation lifetime component of the composite neutron lifetime and may be thought of as the slope of the formation component curve of FIG. 3. Finally, $C_B$ represents the component of the count rate due to the long lived radiation such as tool case and detector activation and the like and may be thought of as a constant component as shown by the horizontal line labelled background in FIG. 3. The composite thermal neutron decay curve shown in FIG. 3 is the resultant or summation of the borehole component, formation component and background component curves illustrated therein.

In the technique of the present invention, the background component $C_B$ is measured during a separate portion of the operating cycle as illustrated in FIG. 4. Referring now to FIG. 4, a telemetry stream from a downhole instrument which will be described in more detail subsequently is shown as a function of time. A synchronization pulse begins each operating cycle of the downhole instrumentation. This synchronization pulse is followed immediately by a neutron burst of approximately constant intensity and having a duration which will be described in more detail subsequently. Four or more time gating intervals follow each neutron burst during which count rate measurements at a detector spaced from the source are made and transmitted to the surface. The multiple time gating intervals are (for statistical purposes) essentially contiguous and last for a total of approximately 700 microseconds following the synchronization pulse. This repetitive operating cycle is repeated approximately 1200 times during a one second interval. At the end of a one second interval, a background gate shown in FIG. 4 is used to count background radiation corresponding to $C_B$ in FIG. 3. During this 55,000 microseconds or 55 milliseconds interval, the neutron generator is not pulsed. Therefore, the measurements made during this time interval, after approximately 5 milliseconds to allow thermal capture radiation following the last sequential neutron burst to decay to a negligible level, will contain only count information due to radiation attributable to background. This background count information is telemetered to the surface by the downhole system and processed as will be described in more detail subsequently.

When the background counting rate $C_B$ is measured in the manner described and telemetered to the surface, it may be subtracted from the composite counting rate C(t) of Equation 3 to obtain a net counting rate C'(t) as given in Equation 4.

$$C'(t) = C(t) - C_B = A_B^{-t/\tau_B} + A_F^{-t/\tau_F} \qquad (4)$$

In Equation 4, the symbols are all as previously defined.

In the method of the present invention, as illustrated with respect to FIGS. 3 and 4, six counting rates measured in the six time gates following the neutron burst and labelled $T_1$, $T_2$, $T_3$, $T_4$, $T_5$, and $T_6$ are combined by an iterative least-squares fitting technique. The counting rate measurements in the six time gates may be fitted in real time in a surface computer, for example, in order to obtain the parameters of interest in Equations 3 and 4. The fitting procedure yields $\tau_F$, $\tau_B$, $A_B$ and $A_F$ as previously defined. It will be observed that the six approximately contiguous time gating intervals illustrated in FIG. 3, have negligible or minimal time delay between each gate to improve statistical repeatability. Therefore, the full counting rate information (following a short moderation time interval) from the end of the neutron burst to the opening of the first time gate, which moderation time is typically of the order of 30–50 microseconds, is utilized in the method of the present invention. No count information is lost due to waiting for a borehole component to decay. Additionally, since this technique simultaneously determines $\tau_F$ and $\tau_B$, the criterion of the Mills, et al paper previously referenced is met in order to determine intrinsic formation $\Sigma$ measurements (ie, a knowledge of borehole parameters).

Referring now to FIGS. 5 and 6, an alternative time gating scheme which employs the techniques of the present invention is illustrated schematically. In FIG. 5, a neutron burst of 10 to 100 microseconds durations is shown, a 20–50 microsecond moderation time interval follows the burst and then a time gate labelled gate 1 is opened for a relatively short duration of time. An equal width (or if desired, a slightly different width) time gate 2 is used. Subsequent time gates 3, 4, 5 and 6 are each of longer duration than their predecessor in the time gating sequence. The aim of this time gating scheme is to statistically optimize the counting rates in each of the gates. As the composite thermal neutron population decay curve falls off, the successively wider time gates allow more counts to occur at the lower counting rate of the later time gates. The actual times contemplated for time gating schemes shown in FIGS. 4 and 6 are given in Tables 1 and 2 which follows. (In Tables 1 and 2 all times are measured with respect to the reference time=0 at the end of the neutron burst).

It should be noted that the actual width of each of the gates described for either gating scheme above is not important except for statistical error minimization or electronics simplification reasons.

TABLE 1

| TIME GATING SCHEME OF FIG. 3 | | | |
|---|---|---|---|
| Gate No. | Start Time | Stop Time | Duration |
| 1 | 50μ sec. | 150μ sec. | 100μ sec. |
| 2 | 150μ sec. | 250μ sec. | 100μ sec. |
| 3 | 250μ sec. | 350μ sec. | 100μ sec. |
| 4 | 300μ sec. | 450μ sec. | 100μ sec. |
| 5 | 450μ sec. | 550μ sec. | 100μ sec. |
| 6 | 550μ sec. | 650μ sec. | 100μ sec. |

TABLE 2

| TIME GATING SCHEME OF FIG. 5 | | | |
|---|---|---|---|
| Gate No. | Start Time | Stop Time | Duration |
| 1 | 50μ sec. | 90μ sec. | 40μ sec. |
| 2 | 110μ sec. | 150μ sec. | 40μ sec. |
| 3 | 170μ sec. | 230μ sec. | 60μ sec. |
| 4 | 230μ sec. | 310μ sec. | 80μ sec. |
| 5 | 310μ sec. | 470μ sec. | 160μ sec. |
| 6 | 470μ sec. | 690μ sec. | 220μ sec. |

It should be realized that short time lapses ($\approx 5$ $\mu$sec.) between the time gates in Tables 1 and 2 may be required to account for time necessary to shift the contents of counters into memory buffers in the downhole tool electronics to be described subsequently.

FIG. 6 illustrates a telemetry stream resulting from the time gating arrangement illustrated in FIG. 5. A synchronization pulse is sent to the surface by the downhole electronics. This is followed by the neutron burst and the reference time begins at the ending of the neutron burst. The short 20-50 microsecond moderation time interval elapses and then a digital number representing the count rates made in time gate 1, labelled $G_1$ in FIG. 6, are telemetered to the surface. Similarly, digital numbers representing the counts in gates 2-6. This sequence is followed for one second. Then the background 5 millisecond delay and 50 milliseconds gating interval is initiated as illustrated previously with respect to FIG. 4. In either event, the counting rates $C(t_i)$ i=1-6 are telemetered to the surface where they are employed in a surface computer (to be described in more detail subsequently) to employ an iterative least-square fitting technique for extracting the parameters of interest.

Since Equation 4 is non-linear it is convenient to use an iterative fitting procedure for the least-squares fit. A particular fitting procedure is illustrated subsequently and will be described in more detail with respect to FIGS. 7a, b and c and FIG. 8. It will suffice to say, however, at this point that the parameters of interest are obtained from the surface computer by a least-square iterative fitting procedure. The values of $\tau_F$, $\tau_B$, $A_F$, and $A_B$ may then be recorded as a function of borehole depth in a conventional manner. It should be pointed out that non-iterative methods to obtain these same four parameters, such as Prony's method, could also be used.

Referring now to FIG. 1, a well logging system in accordance with the concepts of the present invention is illustrated schematically. A well borehole 10 is filled with a borehole fluid 11 and penetrates earth formations 20 to be investigated. A downhole well logging sonde 12 is suspended in the borehole 10 via a conventional armored logging cable 13, in a manner known in the art, such that the sonde 12 maybe raised and lowered through the borehole as desired. The well logging cable 13 passes over a sheave wheel 14 at the surface. The sheave wheel 14 is electrically or mechanically coupled, as indicated by dotted line 15, to a well logging recorder 18 which may comprise an optical recorder, or magnetic tape, or both, as known in the art. The record of measurements made by the downhole sonde 12, may thus be recorded as a function of the depth in the borehole of the sonde 12.

In the downhole sonde 12, a neutron generator 21 is supplied with high voltage (approximately 100 kilovolts) for its operation by a high voltage power supply 22. Control and telemetry electronics 25 are utilized to supply control signals to the high voltage supply and the neutron generator 21 and to telemeter information measured by the downhole instrument to the surface via the logging cable 13.

Longitudinally spaced from the neutron generator 21 are two radiation detectors 23 and 24. Radiations detectors 23 and 24 may comprise, for example, thallium activated sodium iodide crystals which are optically coupled to photomultiplier tubes. The detectors 23 and 24 serve to detect gamma radiation produced in the surrounding formations 20 resulting from the action of the neutron generator 21 in emitting neutrons. A neutron shielding material 28 having a high density matter content or large scattering cross-section is interposed between the neutron generator 21 and the dual spaced detectors 23 and 24, in order to prevent direct irradiation of the detectors by neutrons emitted by the neutron generator 21. Shielding 29 may also be interposed between the detectors 23 and 24 if desired.

Upon activation of the neutron generator 21, a burst, or pulse, of neutrons of approximately 10-100 microseconds duration is initiated and is emitted into the well borehole 10, borehole fluid 11 and, if the borehole is cased, through the steel casing 26 and cement layer 27 surrounding the steel casing into earth formations 20 being investigated. The neutron burst is rapidly moderated or slowed down by scattering interactions such that the neutrons are all essentially at thermal energy. The thermalized or thermal neutrons then being capture interactions with the elemental nuclei of constituents of borehole and the earth formations 20 and pore spaces contained therein.

The capture of neutrons by nuclei of elements comprising the borehole constituents 11, 26, 12, and 27 and the earth formations 20 and their pore spaces produce capture gamma rays which are emitted and impinge upon detectors 23 and 24. A voltage pulse is produced from the photomultipliers of detectors 23 and 24 for each gamma ray so detected. These voltage pulses are supplied to the electronics section 25, counted in a digital counter, and are telemetered to the surface via a conductor 16 of the well logging cable 13. At the surface, a surface electronics package 17 detects the telemetered information from the downhole sonde 12 and performs the iterative least-squares fitting technique to determine the $\tau_F$, $\tau_B$, $A_F$ and $A_B$ with respect to the borehole materials and earth formations 20 being investigated. The surface electronics then supplies signals representative of the measured quantities to the recorder 18 where they are recorded as a function of borehole depth.

Figure 2:
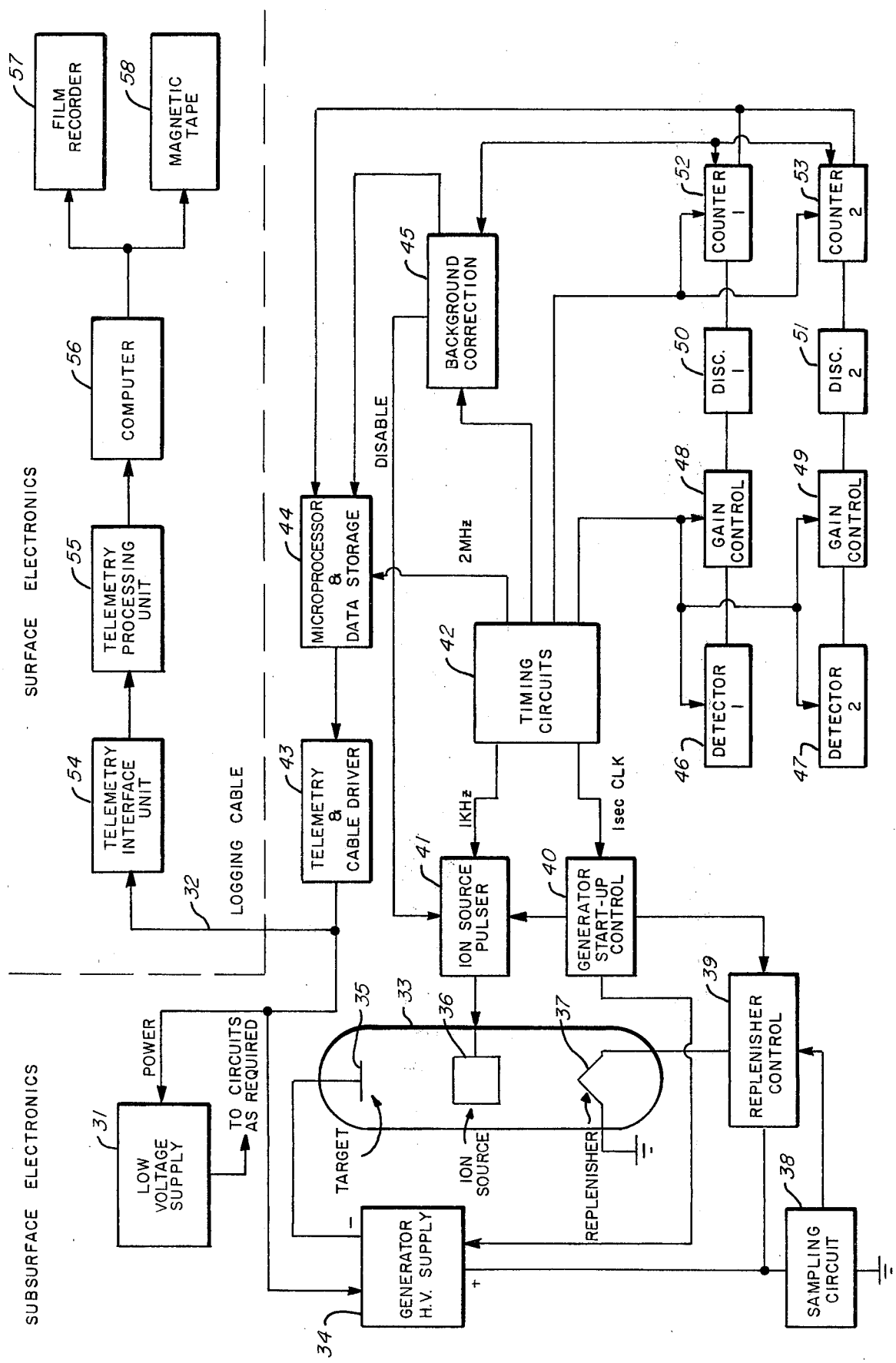
FIG. 2 is a schematic block diagram depicting the electronic systems of the well logging system of the present invention.

Referring now to FIG. 2, a schematic block diagram illustrating the electronic portions of the subsurface and surface electronics systems are illustrated in more detail but still schematically. Power for operation of the subsurface electronics is supplied via a conductor of the well logging cable 32 to a conventional low voltage power supply 31 and a high voltage power supply 34. The high voltage power supply 34 may be of the Cockcroft Walton multiple stage type and supplies approximately, 100 kilovolts for the operation of the neutron generator tube 33. The neutron generator tube 33 is of the deuterium-tritium accelerator type. An ion source 36 which is maintained at a potential near ground is used to generate deuterium-ions from deuterium gas filling the envelope of tube 33. A replenisher heater 37 is impregnated with additional deuterium and maintains a pressure level of deuterium gas inside the tube 33 envelope sufficient to supply ion source 36 with deuterium gas for ionization. A target 35 is impregnated with tritum and is maintained at a relatively high negative 100 kilovolts potential. The ion source is controlled by an ion source pulser 41. When supplied with a relatively low level voltage pulse, the ion source causes gas in the tube 33 envelope to become ionized and accelerated toward the target material 35. Upon impinging on the target material of target 35, the deuterium ions interact thermonuclearly with the tritium ions in the target to produce neutrons, which then are emitted in a generally spherically symmetrical fashion from the neutron generator tube 33 into the borehole and surrounding earth formations.

A replenisher control circuit 39 is supplied with samples of the neutron generator target current by a sampling circuit 38 and utilizes this to compare with a reference signal to control the replenisher current and thereby the gas pressure in the envelope of the neutron generator tube 33. Timing circuits 42 which comprise a master timing oscillator operating at a relatively high frequency and an appropriate divider chain, supplies 1.25 kHZ pulses to the ion source pulser 41, and also supplies one second clock pulses to the neutron generator start-up control circuit 40. Moreover, timing circuit 42 supplies 2 megahertz clock pulses to a microprocessor and data storage array 44 and supplies timing pulses to the background circuit 45 and counters 52 and 53. Similarly, timing signals are supplied to a pair of gain control circuits 48 and 49.

During the background portion of the detection cycle background circuit 45 is supplied with counts from the counters 52 and 53. This circuit also provides a disable pulse to the ion source 41 to prevent pulsing of the neutron generator during the background counting portion of the cycle. The background correction circuit 45 supplies background count information to microprocessor and data storage 44. Background may be stored and averaged for longer periods than capture data since at low discriminator thresholds most gamma ray background is from neutron activation of the iodine in the detector crystal, which has 27 minutes half life.

Better statistics in subtracted signals results. Adaptive filtering, such as that described in the paper "Application of Digital Filtering Techniques to Nuclear Well Logs", Ward Schultz, et al, SPWLA TRANS, June 1981, can also be applied to background and capture gates prior to executing the iterative program.

The digital count information from counters 52 and 53 and background correction circuit 45 are supplied to the microprocessor and data storage circuit 44. These circuits 44 format the data and preset it in a serial manner to the telemetry circuit 43 which is used to telemeter the digital information from the counters and background correction circuit to the surface via well logging cable 32. At the surface, a telemetry interface unit 54 detects the analog telemetry voltage signals from the logging cable 32 conductors and supplies them to a telemetry processing unit 55 which formats the digital count rate information representing the counting rate from counters 52 and 53 in the subsurface equipment in terms of the time gating schemes as previously discussed. The digital numbers representative of the count rates in each of the six time gates and the background counting rate are then supplied to a digital computer 56.

The computer 56 is programmed in accordance with the flow chart of FIGS. 7a, 7b and 7c and FIG. 8 to interpret the six time gates and background counting rate information in terms of the thermal neutron decay time or thermal neutron lifetime of the borehole and formation components from each detector. Output signals representing formation parameters of interest are supplied from the computer 56 to a film recorder 57 and a magnetic tape recorder 58 for recording as a function of borehole depth. The surface computer 56 is programmed in accordance with the flow charts illustrated in FIGS. 7a, 7b, 7c and FIG. 8 to extract the earth formation and borehole components of thermal neutron decay times $\tau_B$ and $\tau_F$, and the intercepts $A_B$ and $A_F$ of FIG. 3 which represent the counting rates at the end of the neutron burst due to the borehole and formation components of thermal neutron population respectively. In order to accomplish this an iterative least squares fitting scheme is utilized.

Figure 7A:
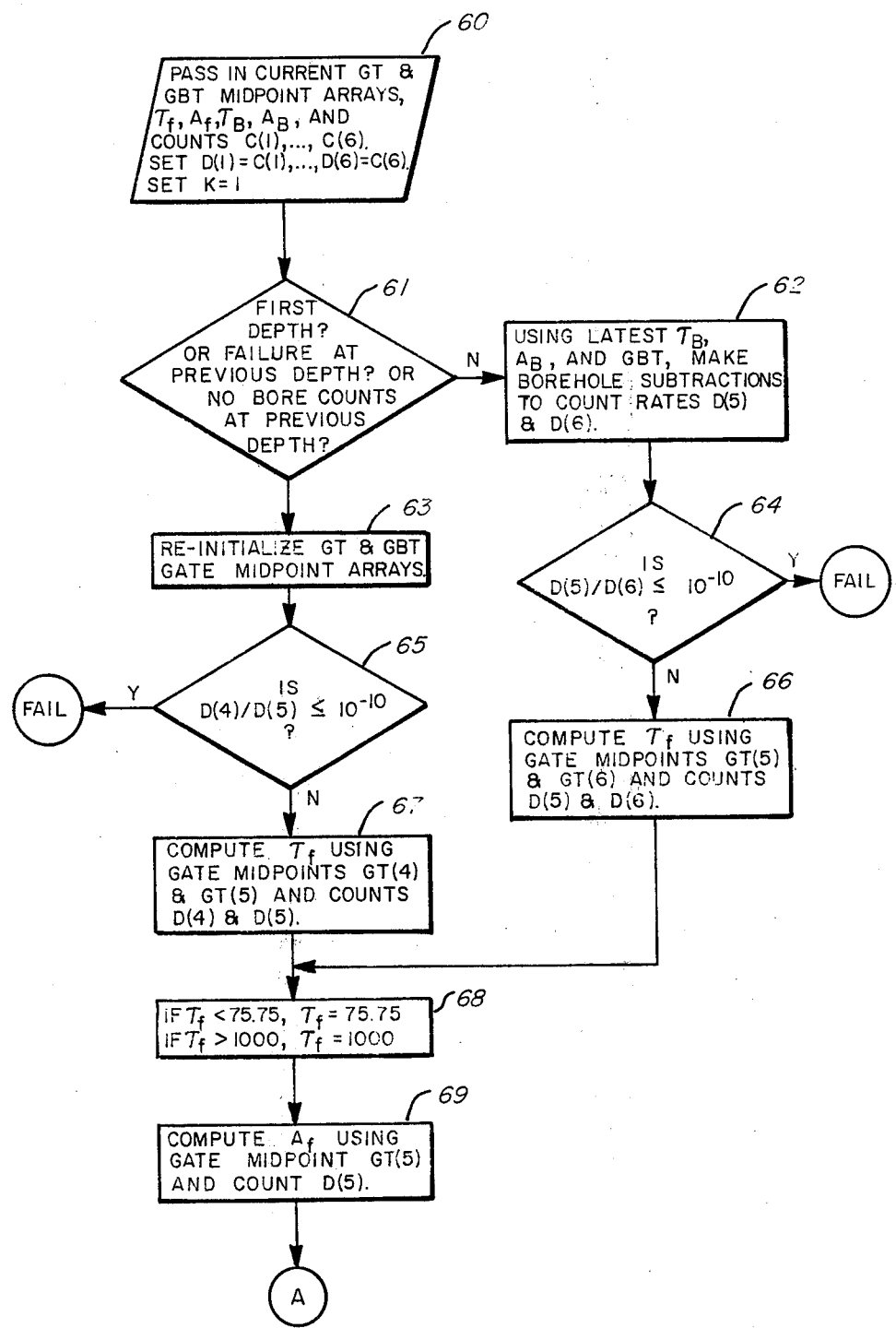
FIGS. 7a, b, and c and FIG. 8 are flow chart diagrams illustrating embodiments of one method for obtaining parameters of interest of earth formations by a surface computer at both near and far detectors.
Figure 7B:
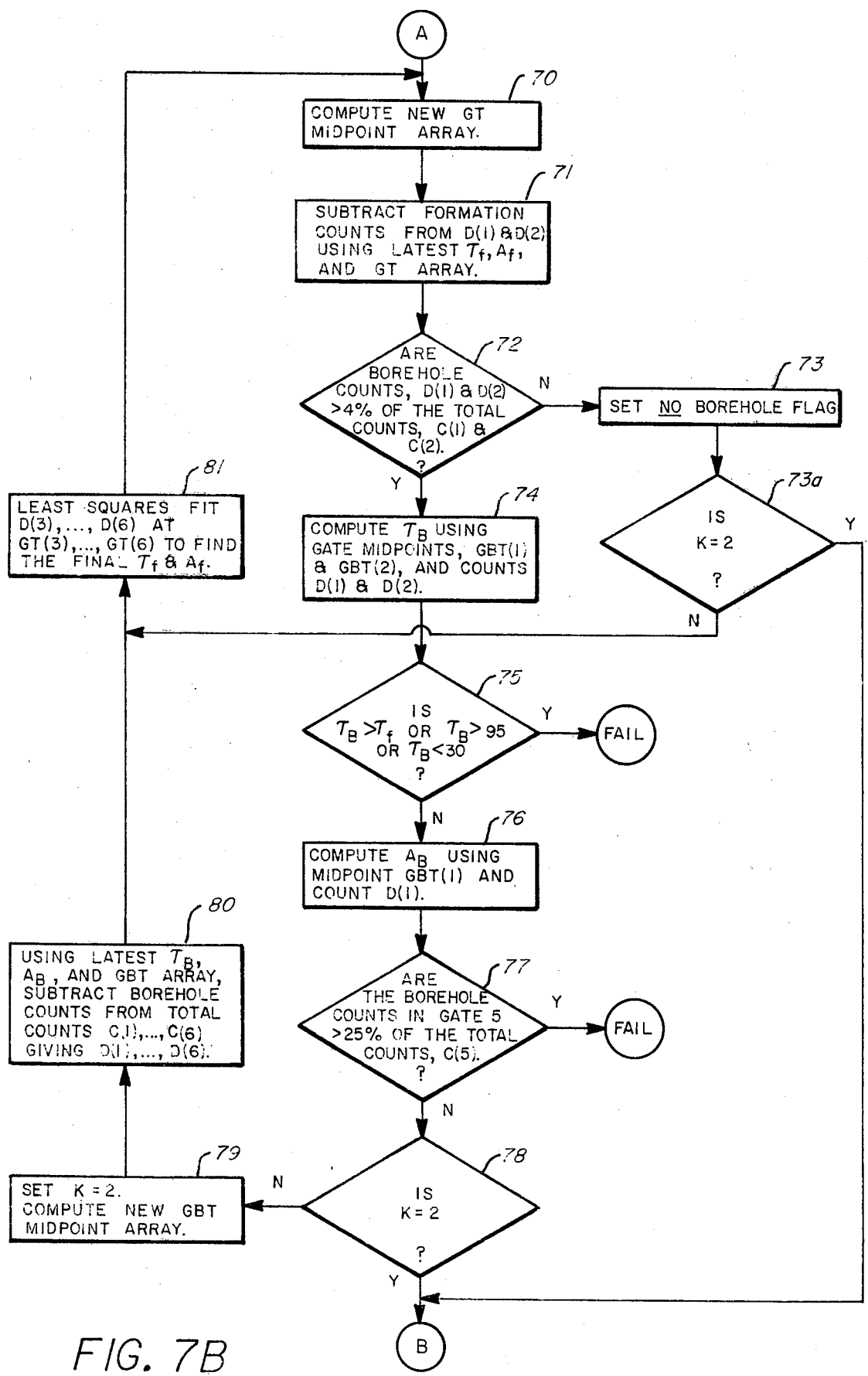
Figure 7C:
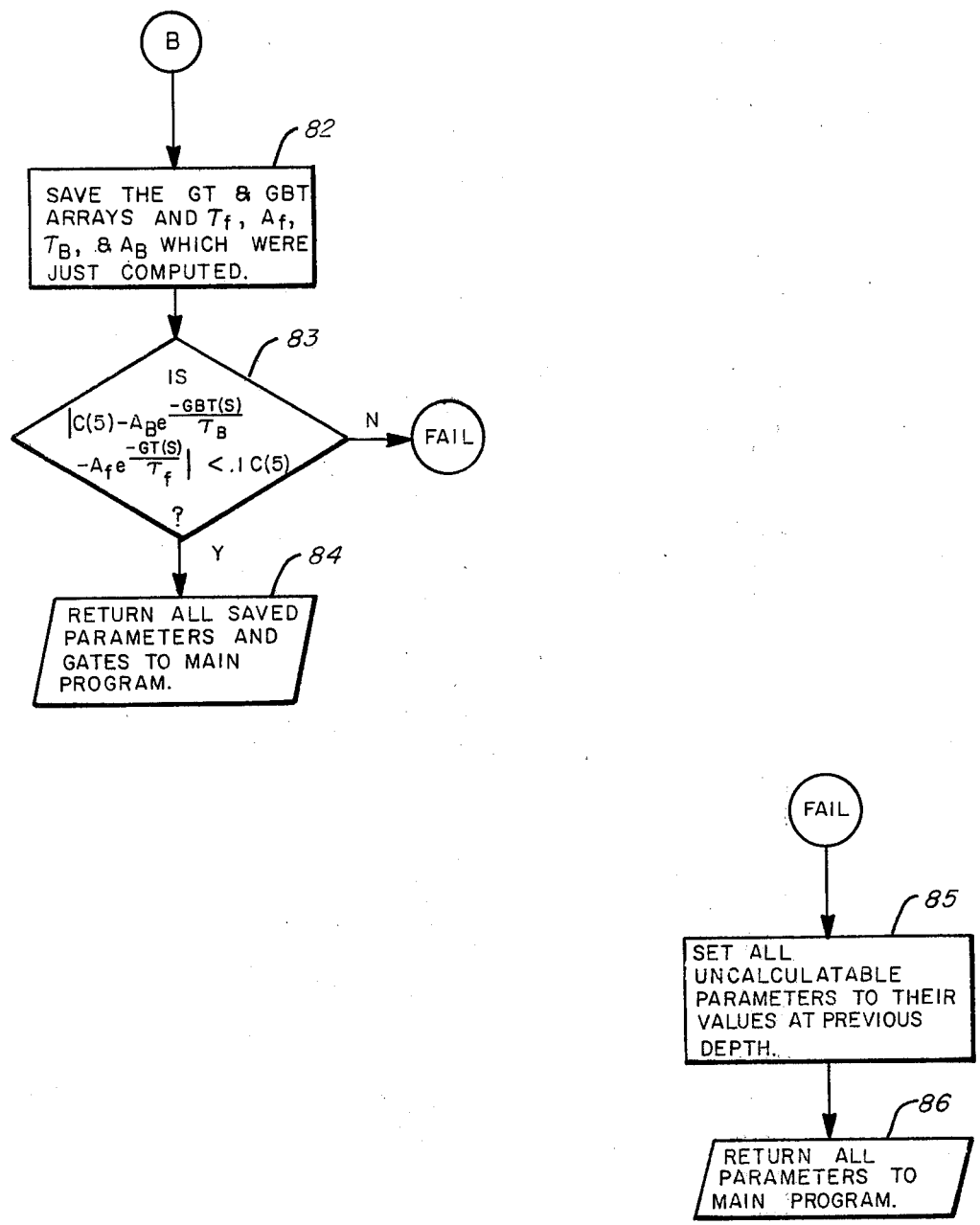

The above referenced iterative scheme for determining the borehole and earth formation decay times is described with more particularity with respect to FIGS. 7a, 7b, 7c and 8. FIGS. 7a, 7b and 7c describes the processing for obtaining this information based on the count rates in the time gates in the near detector, while the flow diagram of FIG. 8 refers to the determination based on the count rates in the corresponding gates for the far detector from the neutron source. It should be mentioned that the exact number of gates used in this scheme is not absolutely crucial as long as it is at least four or greater. The system is designed to work optimally with six gates plus a background gate. However, the time widths of the gates may also be variable, as can any delay between the gates. Thus the gating schemes illustrates in both FIGS. 3 and 5 are susceptible to processing by this technique.

Figure 8:
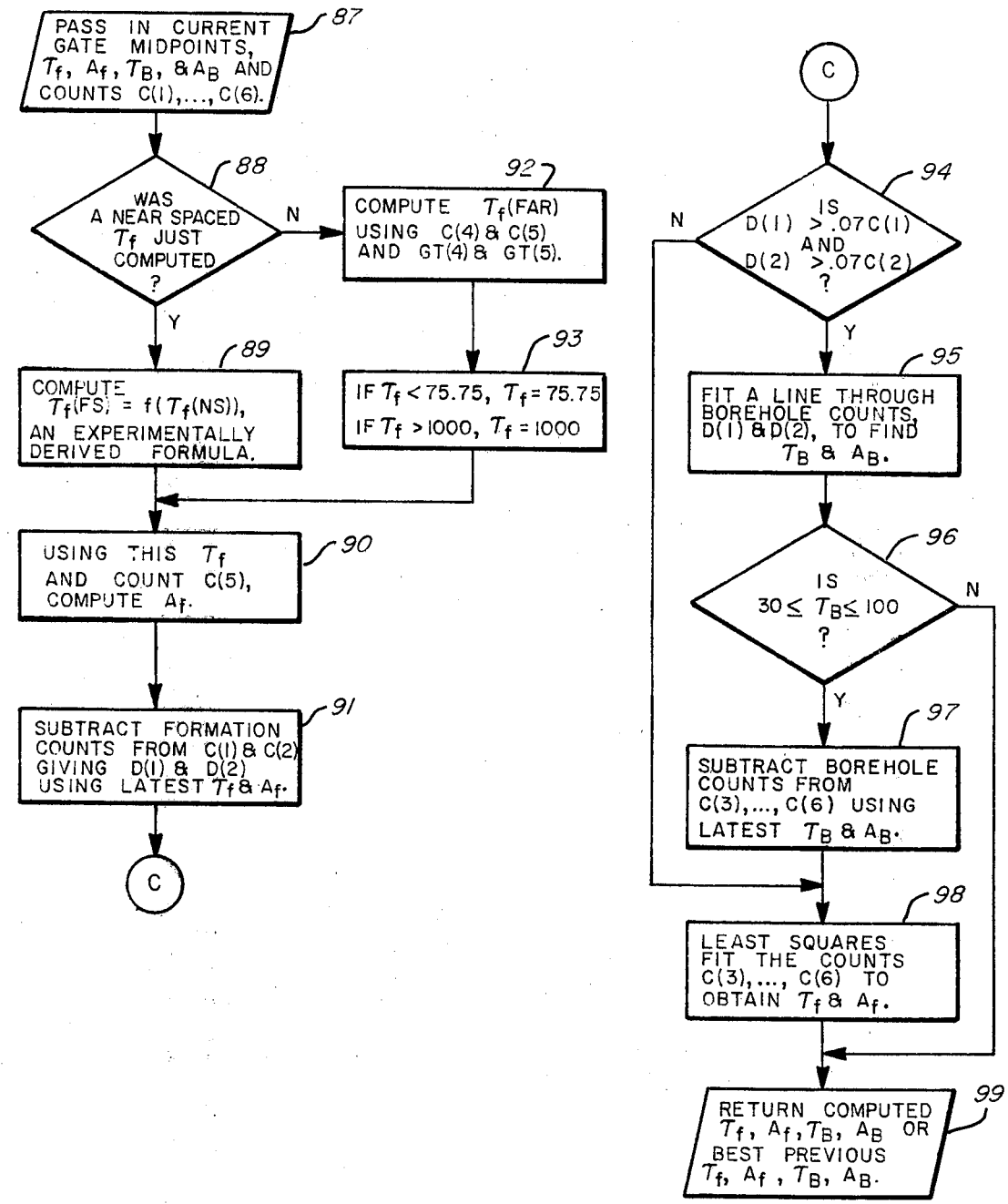

Before discussing the processing of FIGS. 7 and 8 with respect to the flow charts shown therein, a few words about the general philosophy of this processing scheme are in order.

As previously described, data is accumulated in each of the six time gates at each of the dual detectors for approximately one second intervals and transmitted to the surface from the downhole instrument once per one second interval. In addition, a background count is made at each detector for the period indicated previously approximately once per second and this is also transmitted to the surface computer for processing on a once per second basis. Borehole information, after being checked to insure count rates consistency with the next data set, is carried forward from the processing of one data set to the next data set in order to speed up convergence of the formation and borehole $\tau$ measurements. The previous borehole component is subtracted from the new, or just measured data, since borehole conditions are slowly or infrequently varying such as the salinity borehole size, and casing size and weight in cased holes. The carrying forward and subtraction of the borehole data has the effect of improving the first formation parameter calculations on a given data set by carrying forward slowing changing parameters from earlier data sets. This feature coupled with convergence checks and failure options which will be described in more detail with respect to FIGS. 7 and 8 assure accurate measurements of all parameters even under changing borehole conditions. In the long spaced detector, $\tau_F$ data from the near spaced detector, corrected for diffusion effects between the detectors, can be used to initiate and speed up the long spaced $\tau$ convergence process.

Because the gate midpoint adjusting formula depends on a value of $\tau$ and the gate width it is necessary to use two formulae, one which depends on $\tau_B$ and the other which depends on $\tau_F$. Furthermore, since the counting rate is the sum of two relatively independent exponential terms, it is desirable to keep any borehole or formation count rate computations as independent as possible. Therefore, two complete sets of shifted gate midpoints, GT and GBT, are employed and adjusted.

The processing of each new set of data is begun with a two gate formation decay time $\tau_F$ measurement which uses gates remote from the neutron burst. This minimizes the effect of any inaccuracies in borehole data carried forward from previous data sets. These gates, which are remote from the neutron burst, may be up to 250 microseconds duration. This may significantly effect the midpoint shifts of the gate (timewise), if the $\tau_F$ changes significantly. Hence convergence and default options are desirable to insure that convergence will continue across a formation interval change. Subsequent formation decay time or $\tau$ iterations use additional borehole affected gates to improve these statistics, but, only after more accurate borehole subtraction parameters are determined in the processing.

Final decay time $\tau$ and amplitude "A" determinations made from the processing are insured to be reasonable by a sequence of convergence checks. A primary check is made to insure that the total observed counts in a gate reasonably remote from the burst are within a given tolerance of the calculated formation counts. If this or other convergence checks fail, formation and borehole data from the previous data set is output. In another failure default mode (not described below), it is possible to revert back to a $\tau_F$ output based on a two gate slope calculation, using the two gates most remote from the neutron burst, instead of values from the previous data set. In all instances, where failure is detected the next data set uses no carry forward parameters and begins the iteration process with a two gate $\tau_F$ measurement using gates where both midpoint shifts of the gates (timewise) and borehole dependence are minimized.

In a decaying curve the physical midpoint of gate does not occur at the same time as the time at which the average count rate occurs. This average time is used in the $\tau$ calculations and hence a midpoint shift in the gates (a function of $\tau$) must be calculated and applied to each gate.

The required midpoint shifts are carried forward to the next data set for both the borehole and formation $\tau$ for all gates whenever convergence is achieved in any data set. This assures more accurate results when operating on the next data set.

Moreover, a check is made on the statistical significance of the borehole counting rates and hence the $A_B$ and $\tau_B$ which result from such count rates. If the borehole counts are not a reasonable factor larger than statistical errors calculated for the time gates 1 and 2 in which the borehole parameters are calculated, then the borehole counts are ignored in the formation affected time gates and the system outputs nonborehole corrected estimates of $\tau_F$ and $A_F$. If this is not done, then large errors in borehole corrections to counts in remote gates can occur. Hence, erroneous formation parameters could be calculated.

Referring now to FIGS. 7a, b and c, the processing of the measured count rate data in the near detector will be discussed in more detail. The discussion will be in terms of the flow chart of the processing program used in the computer 56 of FIG. 2 which has previously been described generally.

Entry is made to the processing program at Block 60 of FIG. 7a. Current gate time GT and gate borehole time (GBT) midpoint arrays for each of the six time gates and the background time gate together with previously computed $\tau_F$ $A_F$, $\tau_B$, $A_B$ from the previous data set and the gate count rates C(1) through C(6) are input to the program. Control is then passed to logic block 61.

At logic block 61 a test is performed to determine if this is the first data set of a well logging run or if there has been a failure at a previous depth. This failure mode will be explained subsequently in more detail. If either of these conditions exists, then control passes to logic block 63 and the formation gate time and borehole gate time arrays are reinitialized to preset initial value. Control is then passed to logic block 65 where a test is performed to indicate whether the counting rate ratio D(4)/D(5) is less than some arbitrary value (i.e. $10^{-10}$). This test indicates whether significant background corrected count rates exist in gates 4 and 5. If a failure condition occurs control is passed to the fail section which is discussed in more detail in FIG. 7c. Such a failure would indicate that too large a background component exists in time gates which are placed relatively far from the end of the neutron burst indicating some unusual downhole conditions or a large statistical fluctuations.

If the test at block 65 passes, control is transferred to logic block 67 where a new formation decay time $\tau_F$ is computed using preset typical times of gates 4 and 5 and counts D(4) and D(5). Control is then passed to logic block 68.

Returning to logic block 61, if the test there does not fail, no abnormal conditions are indicated, and control is passed to logic block 62. At logic block 62, using the latest borehole decay time parameter $\tau_B$ and amplitude $A_B$ and the borehole component time gate center point GBT, the borehole component of count rate is subtracted from the count rates in gates D(5) and and D(6). Control is then transferred to logic block 64.

At logic block 64 a test is performed to determine the relative magnitude of the borehole corrected count rates in gates 5 and 6. If the ratio of the count rate in gate 5 to 6 (corrected for borehole counts) is less than some arbitrary parameter, control is transferred to the fail section to be discussed with respect to FIG. 7c. This would indicate that not enough formation counts existed in gates 5 and 6 to accurately compute an initial estimate for iteration purposes of the formation decay time $\tau_F$. If the test at block 64 passes, control is transferred to logic block 66.

At logic block 66 a new formation decay time $\tau_F$ is computed from the two points of count rate data contained in gates 5 and 6 and the shifted gate midpoints of these gates (from the previous data set). Control is then transferred to logic block 68.

At logic block 68 the formation decay time just computed in either logic block 66 or 67 is bound limited by testing it to determine if it is below some arbitrary value or above some arbitrary value. If it exceeds the arbitrary values selected, it is simply set to these arbitrary bounding values and control is transferred to logic block 69. At logic block 69 a formation amplitude component $A_F$ is computed using the gate midpoint GT(5) and count D(5). Control is then transferred to logic block 70.

At logic block 70 a new GT gate time midpoint array for each of the six time gates is computed and control is passed to logic block 71.

At logic block 71, the formation component counts appearing in the count rate of gates 1 and 2 are subtracted using the just computed values of $\tau_F$, $A_F$ and the gate midpoint time array. Control is then transferred to logic block 72. At logic block 72, a test is performed to determine if the borehole counts in gates 1 and 2 are greater than 4 percent (an arbitrary parameter based on statistical calculations) of the total counts in gates 1 or 2. This would normally be the case. If it is not the case, control is transferred to logic block 73 where a "no bore" flag is set to indicate a very small borehole component relative to the formation component. If this "no bore" condition holds, control passes to logic block 73(a) where a test is made to determine if both iterations have been completed. If so, control flows to logic block 82 which is discussed subsequently. If the "no bore" condition does not hold, then control is then transferred to logic block 74.

At logic block 74 a value of borehole component decay time $\tau_B$ is computed using the gate midpoint GBT(1) and GBT(2) and counts D(1) and D(2). Control is then transferred to logic block 75.

At logic block 75, a test is performed to determine if the just computed borehole component decay time $\tau_B$ is greater than the computed formation component decay time $\tau_F$, or if the formation component decay time $\tau_B$ exceeds 95 or is less than 30 microseconds (arbitrary range limit values). If either of these tests pass, then control is transferred to the fail section to be discussed in more detail with respect to FIG. 7c. If not, normal conditions are indicated and control is transferred to logic block 76.

At logic block 76, a new borehole component amplitude $A_B$ is computed using the midpoint of timegate 1, GBT(1), and the borehole count rate D(1). Control is then transferred to logic block 77.

At logic block 77, a test is performed to determine if the borehole counts in gates exceed 25 percent (arbitrary limit value) of the total counts in that gate. If they do, this indicates that some unusual condition exists and control is transferred to the fail section to be discussed subsequently. If not, conditions are normal and control is transferred to logic block 78.

At logic block 78, a test is made to determine if the counter indicator K is equal to two. If so, this indicates two iterations have been completed through this portion of the program and control is transferred to logic block 82. If not, only one iteration has been made and control is transferred to logic block 79. At logic block 79, control counter K is set equal two and new gate time midpoint array GBT is computed. Control is then transferred to logic block 80.

At logic block 80, count rate data D(1) through D(6) are updated by subtracting borehole component counts from the count rate data from the downhole instrument C(1) through C(6), using the just computed borehole amplitude component $A_B$ and gate time array GBT. Control is then transferred to logic block 81.

At logic block 81, the least-squares fit is performed as previously discussed to compute a formation decay time $\tau_F$ and formation amplitude component $A_F$. Control is then transferred back to logic block 70 where the second iteration is followed through to compute an improved estimate of the borehole components as previously discussed.

Referring now to logic block 82, when the iterative procedure previously described in FIG. 7b is completed, as indicated by the test on counter K at logic block 78, the borehole and formation parameters $A_F$, $A_B$, $\tau_F$ and $\tau_B$ have been computed. Along with this, gate midpoint times are computed and these arrays are saved for the next pass through the processing scheme for the near detector. Control is then transferred to logic block 83.

A convergence test is performed at block 83 to determine if these parameters $A_B$, $A_F$, $\tau_F$, $\tau_B$ and the gate midpoint time arrays are reasonable by comparing these with a percentage of the count rates from the downhole tool in a remote (the fifth) timegate. If this test fails control is transferred to the fail section. If the test passes then reasonable values for the near detector have been computed and control is returned to the control program for processing of the far spaced detector count rate data.

Referring now to FIG. 7c the fail section is entered from any of the previously discussed points at which some failure is indicated. In this case control is transferred to logic block 85 where all uncalculable parameters are set to their value at the previous depth. In an alternate mode $A_F$ and $\tau_F$ are not set to previous values, but rather to those obtained by a conventional 2 gate $\tau_F$ measurement using remote gate observed count rates C(5) and C(6), and their shifted midpoints in the GT array. These values, and a failure reset parameter, are then returned to the main control program at logic block 68 for use in the next processing period. In the event of failure, no borehole parameters or gate shifts are used in processing the next data set. When the near detector processing is completed at logic block 84, control is normally transferred to logic block 87 for processing of the far spaced detector count rate data. The processing of the far spaced detector data is similar to that of the processing of the near spaced detector data but maybe more readily appreciated by reference to FIG. 8.

At logic block 87 of FIG. 8, current gate midpoint arrays and formation decay time and amplitude and borehole decay and amplitude information together with the just measured far spaced count rates C(1)

through C(6) are entered through the main control program to the processing program. Control is then transferred to logic block 88.

A test is performed at logic block 88 to determine if a near spaced formation decay time $\tau_F$ was just computed (ie, no failure detected). If a failure was observed, control is transferred to logic block 92 where an initial formation $\tau_F$ for the far detector is computed using the count rates C(4) and C(5) together with gate midpoints GT(4) and GT(5). Control is then transferred to logic block 93 where upper and lower bound test are performed on the just computed formation decay time $\tau_F$ and limiting of this value is accomplished. Control is then transferred to logic block 90. If the test at logic block 88 passes successfully (ie. for initial $\tau_F$ calculations on far spaced detector when good short spaced data was obtained) control is transferred to logic 89 where a different approximation is used to initialize the computation of a far detector formation decay time $\tau_F$. This uses diffusion related empirical formula relating $\tau_F$ far spaced to $\tau_F$ near spaced which was derived by observing the relationship between near and far spaced $\tau_F$ over a wide range of borehole sizes, borehole salinities, and porosities. Control is then transferred to logic block 90.

At logic block 90, the just computed formation decay time $\tau_F$ and the count rate in gate 5, C(5) is used to compute the formation amplitude component $A_F$. Control is then transferred to logic block 91. At logic block 91, the formation count rates are subtracted from the count rates in gates 1 and 2, C(1) and C(2), to give borehole count rates D(1) and D(2). Control is then transferred to logic block 94.

At logic block 94, a test is performed to determine if the borehole count rates D(1) and D(2) are statistically significant. If this test indicates that no statistically significant borehole counts are present, then control is transferred to logic block 98 where the least-squares fit of counts C(3) through C(6) are used to obtain a formation decay $\tau_F$ and amplitude $A_F$ without correcting for borehole counts. If the test at logic block 94 indicates significant borehole count rates, control is transferred to logic block 95.

At logic block 95, a line is fitted through borehole counts D(1) and D(2) to compute a value of the borehole decay time $\tau_B$ and the borehole component amplitude $A_B$. Control is then transferred to logic block 96.

At logic block 96, a test is performed to determine if the borehole decay time $\tau_B$ is between 30 and 100 microseconds (arbitrary typical range limit values). If this condition exists, then the borehole count rate just calculated is subtracted from the count rates in gates C(3) through C(6) using the just computed borehole component decay time and amplitude components, and the least-squares fit of counts C(3) through C(6) is performed to compute $\tau_F$ and $A_F$. These computed values are passed back to the main program. If the borehole component decay time (as indicated by the test at logic block 96) does not fall within the reasonable range, then control is transferred to logic block 99 where control is returned to the main program controlling the computer and the $\tau_F$, $\tau_B$, $A_F$ and $A_B$ (either calculated or best previous) are returned to be output on the log. No long spaced parameters are carried forward to the next cycle.

It should be pointed out that an alternate long spaced processing scheme to the one described above could include an exact duplicate of the short spaced procedure, maintaining total independence between the two detectors calculations.

In the foregoing manner, it is thus seen that optimum use of the count rate information from previous measurement cycles are used to achieve more accurate borehole and formation parametes by achieving accurate early guesses of slowly varying parameters. In the far spaced detector, short spaced diffusion corrected $\tau_F$ values are used to initiate the long spaced $\tau_F$ calculation. When sudden variations occur, tests are always performed to assure that the process is converging and is producing reasonable values for both the formation and borehole components which are sought to be measured with the system of the invention. Using the processing scheme just arrived it has been found possible to compute both formation and borehole components in real time during the measurement process. Thus, the advantages previously described of the neutron lifetime or decay time logging system of the present invention may be realized in an optimum manner.

While the foregoing descriptions may make other alternative embodiments of the invention apparent to those skilled in the art, the subject invention is defined by the appended claims. It is the aim of these claims to cover all such changes and modifications which may be within the true spirit and scope of the invention.

We claim:

1. A method for simultaneously determining the borehole component and the formation component of thermal neutron decay time of a borehole and earth formations in the vicinity of the borehole, comprising the steps of:

repetitively emitting, in a well borehole, relatively short duration pulses of fast neutrons which are rapidly moderated by interaction with nuclei of materials in the borehole and surrounding earth formations and slowed down to thermal energy, creating repetitive bursts of thermal neutron population in the borehole and surrounding earth formations;

detecting, in the borehole during a time interval between said repetitive pulses of fast neutrons, radiations representative of the thermal neutron population in the borehole and surrounding earth formations, in at least four time subintervals subsequent to a pulse of fast neutrons and generating at least four count rate signals representative of said thermal neutron populations during said at least four time subintervals;

detecting, during a separate time interval between said repetitive bursts of fast neutrons, radiations attributable to a background radiation component of radiation and generating a background count signal representative thereof;

correcting said at least four count rate signals for the presence of said background radiation component to provide at least four background corrected count rate signals;

combining said at least four background corrected count rate signals according to an iterative fitting technique in which exponential relationships are assumed to exist for a borehole and a formation component of thermal neutron decay time to simultaneously obtain two measurement signals representative of the borehole component and the formation component of thermal neutron decay times; and recording said measurement signals as a function of borehole depth.

2. The method of claim 1 and further including the step of correcting said at least four count rate signals and said background count signal for system dead time extant in the radiation detecting step.

3. The method of claim 1 wherein at least six time subintervals subsequent to each neutron burst are used in the detecting step.

4. The method of claim 3 wherein said combining step includes a least-squares fitting technique to an exponential relationship assumed to exist for said borehole and formation components of thermal neutron decay time in said iterative fitting technique.

5. The method of claim 4 wherein each of the steps is performed at a plurality of different depths in a well borehole and a recording of said at least two measurement signals is made for each of said plurality of depths in the borehole.

6. The method of claim 1 wherein said emitting and detecting steps are repeated approximately 1200 times per second.

7. The method of claim 1 and further including in the step of combining said at least four count rate signals, simultaneously deriving in said iterative fitting technique at least two additional measurement signals representative of the initial thermal neutron population following a repetitive neutron pulse in the borehole and in the formation media surrounding the borehole.

8. The method of claim 1 wherein detecting steps are initiated after a time sufficient to allow neutron moderation in borehole and formation.

9. The method of claim 8 wherein said detecting steps are initiated approximately 20 to 50 microseconds subsequent to each such neutron pulse, and said at least four time subintervals extend substantially over the entire time interval until the next of said repetitive neutron pulses.

10. The method of claim 8 wherein said at least four time subintervals are of approximately equal duration.

11. The method of claim 8 wherein said at least four time subintervals are each of subsequent greater or equal duration than its predecessor time subinterval.

12. The method of claim 1 wherein said at least four time subintervals are selected such that at least two subintervals maximize the borehole component count rate and at least two such subintervals minimize the borehole component count rate.

13. The method of claim 12 wherein said subinterval selection is optimized by minimizing the duration of the fast neutron pulse.

14. The method of claim 1 wherein the steps are performed repetitively at different borehole depths.

15. The method of claim 14 wherein the borehole component measurement signal from a previous repetition is subtracted from subsequent repetition count rate signals and thereby used to speed up convergence of said iterative fitting technique taking account of slowly varying borehole conditions.

16. The method of claim 1 wherein the detecting step is performed simultaneously at each of two longitudinally spaced locations in a well borehole and the combining step is performed for count rate signals at each such locations.

17. The method of claim 16 wherein measurement signals derived from count rate signals at one such longitudinally spaced location are used to speed up convergence of the iterative technique applied to count rate signals at the second longitudinally spaced location.

18. The method of claim 17 wherein $\tau_F$ from short spaced detector is corrected for diffusion effects and used as an initial estimate of $\tau_F$ in a long spaced detector.

19. A method for simultaneously measuring the borehole component and the formation component of thermal neutron decay times of a borehole and earth formation in the vicinity of the borehole, comprising the steps of:

repetitively emitting, in a well borehole, relatively short duration pulses of fast neutrons which are rapidly moderated by interaction with nuclei of materials in the borehole and surrounding earth formations and slowed down to thermal energy, creating repetitive bursts of thermal neutron population in the borehole and surrounding earth formations;

detecting at least at two different longitudinally spaced locations in the borehole during a time interval between said repetitive pulses of fast neutrons, radiations repesentative of the thermal neutron population in the borehole and surrounding earth formations, in at least four time subintervals subsequent to a pulse of fast neutrons and generating, at each of said at least two longitudinally spaced locations in the borehole, at least four count rate signals representative of said thermal neutron populations during said at least four time subintervals;

combining said at least four count rate signals at each of said at least two differently longitudinally spaced locations in the borehole according to an iterative fitting technique in which exponential relationships are assumed to exist for a borehole component and a formation component of thermal neutron decay time to simultaneously obtain two measurement signals at each of said at least two longitudinally spaced locations representative of the borehole component and the formation component of thermal neutron decay times at said longitudinal locations; and recording said measurement signals as a function of borehole depth.

20. The method of claim 19 and further including the steps of detecting at each of said longitudinally spaced locations, during a separate time interval between said repetitive bursts of fast neutrons, radiations attributable to a background component of radiation at each of said longitudinally spaced locations and generating background count signals representative thereof; and correcting said at least four count rate signals at each of said longitudinally spaced locations for the presence of said background radiation component to provide at least four background corrected count rate signals at each of said longitudinally spaced locations.

21. The method of claim 20 wherein said combining step is performed using said background corrected count rate signals at each of said longitudinally spaced locations.

22. The method of claim 19 wherein at least six time subintervals subsequent to each neutron pulse are used in the detecting step.

23. The method of claim 19 wherein said combining step includes a least squares fitting technique to exponential relationships assumed to exist for said borehole and formation components of thermal neutron decay time.

24. The method of claim 19 wherein each of the steps are performed at a plurality of different depths in a well borehole and produces a log of said measurement signals as a function of borehole depth.

25. The method of claim 19 wherein said emitting and detecting steps are repeated approximately 1200 times per second.

26. The method of claim 19 and further including the step of combining said at least four count rate signals at each of said longitudinally spaced locations to derive at least two additional measurement signals representative of the amplitude of said borehole and said formation components of thermal neutron population at each such longitudinally spaced location.

27. The method of claim 19 wherein the detecting steps are initiated after a time sufficient to allow neutron moderation in the borehole and formation.

28. The method of claim 27 wherein the detecting steps are initiated approximately 20 to 50 microseconds subsequent to each neutron pulse and said at least four time subintervals extend over substantially the entire time interval until the next of said repetitive neutron pulses.

29. The method of claim 28 wherein said at least four time subintervals are of approximately equal duration.

30. The method of claim 28 wherein said at least four time subintervals are each of subsequent greater or equal duration than its predecessor time subinterval.

31. The method of claim 19 wherein the borehole component measurement signals from a previous repetition is subtracted from a subsequent repetition count rate signals and thereby used to speed up convergence of said iterative fitting technique taking account of slowing varying borehole conditions.

32. The method of claim 19 wherein measurement signals derived from count rate signals at one of said different longitudinally spaced locations are used to speed up convergence of the iterative technique applied to count rate signals at the second different longitudinally spaced location.

33. A method for simultaneously measuring the borehole and formation components of thermal neutron decay time of a borehole and earth formations in the vicinity of the borehole, comprising the steps of:
repetitively emitting, in a well borehole, relatively short duration pulses of fast neutrons which are rapidly moderated by interaction with nuclei of materials in the borehole and surrounding earth formations and slowed down to thermal energy, creating repetitive bursts of thermal neutron population in the borehole and surrounding earth formations;
detecting in the borehole during a time interval between said repetitive pulses of fast neutrons, radiations representative of the thermal neutron population in the borehole and surrounding earth formations in at least four time subintervals subsequent to a pulse of fast neutrons and generating at least four count rate signals representative of said thermal neutron populations during said at least four time subintervals;
combining said at least four count rate signals according to a predetermined relationship in which exponential relationships are assumed to exist for a borehole and a formation component of thermal neutron decay time to simultaneously obtain two measurement signals representative of the borehole component and the formation component of thermal neutron decay time; and
recording said measurement signals as a function of borehole depth.

34. The method of claim 33 wherein said combining step is performed according to an iterative technique.

35. The method of claim 33 and further including the steps of detecting during a separate time interval between said repetitive bursts of fast neutrons, radiations attributable to a background radiation component and generating a background count signal representative thereof; and
correcting said at least four count rate signals for the presence of said background radiation component to provide at least four background corrected count rate signals.

36. The method of claim 35 wherein said combining step is performed using said background corrected count rate signals.

37. The method of claim 33 wherein at least six time subintervals subsequent to each neutron pulse are used in the detecting step.

38. The method of claim 33 wherein said combining step includes a least squares fitting technique to exponential relationships assumed to exist for said borehole and formation components of thermal neutron decay time.

39. The method of claim 33 wherein the steps are performed at a plurality of different depths in a well borehole and produces a log of said measurement signals as a function of borehole depth.

40. The method of claim 33 wherein said emitting and detecting steps are repeated approximately 1200 times per second.

41. The method of claim 33 and further including the step of combining said at least four count rate signals to derive at least two additional measurement signals representative of the amplitude of said borehole and said formation components of thermal neutron population.

42. The method of claim 33 wherein the detecting step is initiated after a time sufficient to allow neutron moderation in the borehole and formation.

43. The method of claim 42 wherein the detecting steps are initiated approximately 20 to 50 microseconds subsequent to each neutron pulse and said at least four time subintervals extend over substantially the entire time interval until the next of said repetitive neutron pulses.

44. The method of claim 33 wherein said at least four subintervals are chosen such that at least two subintervals maximize borehole component counts and at least two others minimize borehole component counts.

45. The method of claim 44 wherein said subinterval selection is optimized by minimizing the duration of the fast neutron pulse.

46. The method of claim 44 wherein said at least four time subintervals are of approximately equal duration.

47. The method of claim 44 wherein said at least four time subintervals are each of subsequent greater or equal duration than its predecessor time subinterval.

48. The method of claim 33 wherein the steps are performed at each of at least two different longitudinally spaced locations in a well borehole.

49. The method of claim 33 wherein said combining step utilizes borehole and formation component parameters carried forward in time from previous measurement gates.

* * * * *